(12) United States Patent
Glusker et al.

(10) Patent No.: US 7,516,741 B2
(45) Date of Patent: Apr. 14, 2009

(54) AEROSOLIZATION APPARATUS WITH FEEDBACK MECHANISM

(75) Inventors: Mark J. Glusker, San Mateo, CA (US); Jeff R. Wood, Mountain View, CA (US); John D. Burr, Redwood City, CA (US)

(73) Assignee: Novartis AG

( * ) Notice: Subject to any disclaimer, the term of this patent is extended or adjusted under 35 U.S.C. 154(b) by 65 days.

(21) Appl. No.: 10/704,160

(22) Filed: Nov. 7, 2003

(65) Prior Publication Data

US 2005/0051166 A1    Mar. 10, 2005

Related U.S. Application Data

(60) Provisional application No. 60/431,383, filed on Dec. 6, 2002.

(51) Int. Cl.
*A61M 11/00* (2006.01)

(52) U.S. Cl. .............................. 128/203.21; 128/205.21

(58) Field of Classification Search ............ 128/203.21, 128/203.12, 203.15, 203.19, 203.25, 203.23, 128/203.24, 200.14, 200.24, 205.21; 604/58
See application file for complete search history.

(56) References Cited

U.S. PATENT DOCUMENTS

| | | | |
|---|---|---|---|
| 3,921,637 A * | 11/1975 | Bennie et al. .......... 128/203.15 |
| 3,991,761 A | 11/1976 | Cocozza | |
| 4,114,615 A | 9/1978 | Wetterlin | |
| 4,116,195 A * | 9/1978 | James ........................ 604/244 |
| 4,338,931 A | 7/1982 | Cacazza | |
| 4,344,436 A * | 8/1982 | Kubota ........................ 604/264 |
| 4,846,876 A | 7/1989 | Draber et al. | |
| 5,458,135 A | 10/1995 | Patton et al. | |
| 5,619,985 A | 4/1997 | Ohki et al. | |
| 5,785,049 A | 7/1998 | Smith et al. | |
| 5,922,675 A | 7/1999 | Baker et al. | |
| 6,257,233 B1 | 7/2001 | Burr et al. | |
| 6,357,490 B1 | 3/2002 | Johnston et al. | |
| 6,684,880 B2 * | 2/2004 | Trueba ................... 128/200.16 |
| 6,705,313 B2 * | 3/2004 | Niccolai ................. 128/203.21 |

FOREIGN PATENT DOCUMENTS

| | | |
|---|---|---|
| WO | 95/24183 | 9/1995 |
| WO | 96/32096 | 10/1996 |
| WO | 96/32149 | 10/1996 |
| WO | 99/16419 | 4/1999 |
| WO | 99/16422 | 4/1999 |
| WO | 00/07572 | 2/2000 |
| WO | 00/72904 | 12/2000 |

* cited by examiner

*Primary Examiner*—Steven O Douglas
(74) *Attorney, Agent, or Firm*—Michael Mazza; John W. Kung; Sandra Shim (57) ABSTRACT

An aerosolization apparatus comprises a housing defining a chamber having an air inlet and an air outlet, wherein the chamber is sized to receive a capsule containing a pharmaceutical formulation. A puncturing member is moveable within the chamber to contact the capsule and to provide an opening in the capsule, and a feedback mechanism provides an indication, such as a tactile indication, to a user when the puncturing member has been moved to a position where it provides the opening into the capsule. When air flows through the inlet, the pharmaceutical formulation is aerosolized and the aerosolized pharmaceutical formulation is delivered through the outlet.

24 Claims, 4 Drawing Sheets

AEROSOLIZATION APPARATUS WITH FEEDBACK MECHANISM

This application claims the benefit of U.S. Provisional Patent Application Ser. No. 60/431,383, filed on Dec. 6, 2002, which is incorporated herein by reference in its entirety.

BACKGROUND

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before they caosolized pharmaceutical formulation is orally or nasally inhaled by a patient to deliver the formulation to the patient's respiratory tract, has proven to be a particularly effective and/or desirable alternative. For example, in one inhalation technique, an aerosolized pharmaceutical formulation provides local therapeutic relief to a portion of the respiratory tract, such as the lungs, to treat diseases such as asthma, emphysema, and cystic fibrosis. In another inhalation technique, a pharmaceutical formulation is delivered deep within a patient's lungs where it may be absorbed into the blood stream. Many types of inhalation devices exist including devices that aerosolize a dry powder pharmaceutical formulation.

One type of inhalation device aerosolizes a pharmaceutical formulation that is stored in a capsule. For example, a dose or a portion of a dose of a dry powder pharmaceutical formulation may be stored in a capsule, and the capsule may be inserted into an aerosolization device which is capable of aerosolizing the pharmaceutical formulation. The aerosolization may be accomplished by releasing stored energy. For example, the aerosolization may be accomplished by utilizing energy supplied during the user's inhalation, such as the flow of inhaled air, to aerosolize the pharmaceutical formulation.

Before, during or after being inserted into the aerosolization device, the capsule is opened to expose the pharmaceutical formulation. The opening of the capsule may be performed, for example, by puncturing the capsule, tearing the capsule, or separating the parts of the capsule.

When the capsule is properly opened and when aerosolization energy is supplied, the pharmaceutical formulation is aerosolized so that it may be inhaled by the user and a dose or portion of a dose of the aerosolized pharmaceutical formulation may be delivered to the user's respiratory tract.

However, improper use of the aerosolization device may result in the delivery of less than the desired amount of the pharmaceutical formulation. For example, if a capsule is not properly or completely opened before the aerosolization process, the amount of pharmaceutical formulation being aerosolized may be reduced or the flow of the aerosolized pharmaceutical formulation may not be of sufficiently high quality to deliver a desirable amount to the user. This improper opening is particularly prevalent when a user is unable or unwilling to visually inspect the opening of the capsule. The user may then unknowingly inhale less than a desired amount of the pharmaceutical formulation.

Therefore, it is desirable to be able to provide an indication to a user of an aerosolization device that a receptacle, such as a capsule containing an inhaleable pharmaceutical formulation, has been properly opened. It is further desirable to be able to provide such indication through a sensory channel used to by the user during the opening process. It is still further desirable to provide an indication to the user without interfering with the aerosolization capabilities of the device.

SUMMARY

The present invention satisfies these needs. In one aspect of the invention, a feedback mechanism provides the user of an aerosolization apparatus an indication that a capsule in the apparatus has been punctured.

In another aspect of the invention, an aerosolization apparatus comprises a housing defining a chamber having an air inlet and an air outlet, wherein the chamber is sized to receive a capsule containing a pharmaceutical formulation; a puncturing member moveable within the chamber to contact the capsule and to provide an opening in the capsule; and a feedback mechanism that provides an indication to a user when the puncturing member has been moved to a position where it provides the opening into the capsule, whereby when air flows through the inlet, the pharmaceutical formulation is aerosolized and the aerosolized pharmaceutical formulation is delivered through the outlet.

In another aspect of the invention, an aerosolization apparatus comprises a body defining a chamber having an air inlet and an air outlet, wherein the chamber is sized to receive a capsule containing a pharmaceutical formulation in a manner which allows the capsule to move within the chamber; a puncturing member moveable within the chamber to contact the capsule and to provide an opening in the capsule; and a feedback mechanism that provides an indication to a user when the puncturing member has been moved to a predetermined position, whereby when a user inhales, air enters into the chamber through the inlet so that the pharmaceutical formulation is aerosolized within the chamber and the aerosolized pharmaceutical formulation is delivered to the user through the outlet.

In another aspect of the invention, a method of providing an aerosolized pharmaceutical formulation comprises providing a aerosolization apparatus comprising a housing which defines a chamber, the chamber being sized to receive a capsule containing a pharmaceutical formulation, the aerosolization apparatus further comprising a feedback mechanism that provides an indication when the capsule has been punctured; and aerosolizing the pharmaceutical formulation when a user inhales by causing air to flow through an inlet in the housing, within the chamber, and through an outlet in the housing to provide the aerosolized pharmaceutical formulation to the user.

In another aspect of the invention, a method of aerosolizing a pharmaceutical formulation comprises providing a capsule containing a pharmaceutical formulation in a chamber in a housing; advancing a puncture member to create an opening in the capsule; receiving an indication when the opening in the capsule is created; and inhaling through an opening in the housing to cause air to flow into the chamber through an inlet in the housing thereby aerosolizing the pharmaceutical formulation.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to a powder aerosolization apparatus. In particular, the invention relates to an aerosolization apparatus capable of aerosolizing a powder contained in a capsule. Although the process is illustrated in the context of aerosolizing a dry powder pharmaceutical formulation for inhalation, the present invention can be used in other processes and should not be limited to the examples provided herein.

Figure 1A:
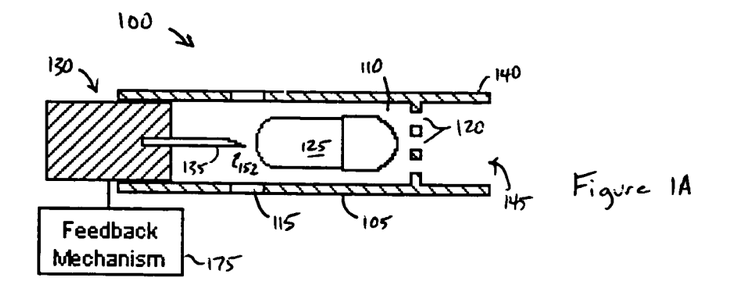
FIG. 1A is a schematic sectional side view of a version of an aerosolization apparatus in a rest position.

An aerosolization apparatus 100 according to the present invention is shown schematically in FIG. 1A. The aerosolization apparatus 100 comprises a housing 105 defining a chamber 110 having one or more air inlets 115 and one or more air outlets 120. The chamber 110 is sized to receive a capsule 125 which contains an aerosolizable pharmaceutical formulation. A puncturing mechanism 130 comprises a puncture member 135 that is moveable within the chamber 110. Near or adjacent the outlet 120 is an end section 140 that may be sized and shaped to be received in a user's mouth or nose so that the user may inhale through an opening 145 in the end section 140 that is in communication with the outlet 120.

The aerosolization apparatus 100 utilizes air flowing through the chamber 110 to aerosolize the pharmaceutical formulation in the capsule 125. For example, FIGS. 1A through 1E illustrate the operation of a version of an aerosolization apparatus 100 where air flowing through the inlet 115 is used to aerosolize the pharmaceutical formulation and the aerosolized pharmaceutical formulation flows through the outlet 120 so that it may be delivered to the user through the opening 145 in the end section 140. The aerosolization apparatus 100 is shown in its initial condition in FIG. 1A. The capsule 125 is positioned within the chamber 110 and the pharmaceutical formulation is secured within the capsule 125.

Figure 1B:
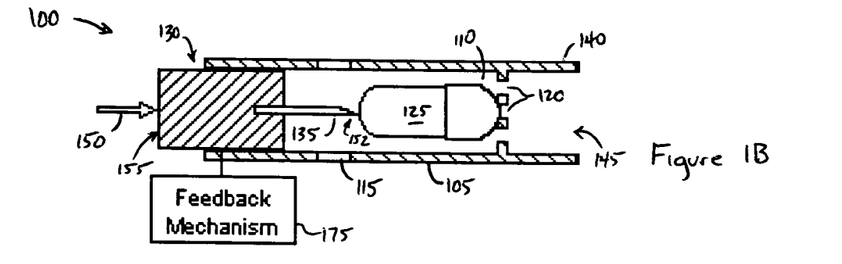
FIG. 1B is a schematic sectional side view of the version of an aerosolization apparatus shown in FIG. 1A just before capsule puncture.
Figure 1C:
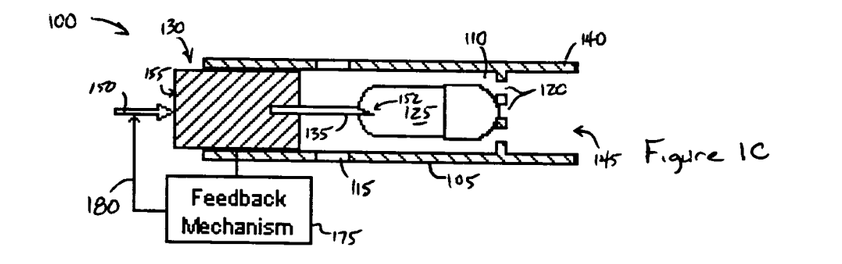
FIG. 1C is a schematic sectional side view of the version of an aerosolization apparatus shown in FIG. 1A as the capsule is being punctured.
Figure 1D:
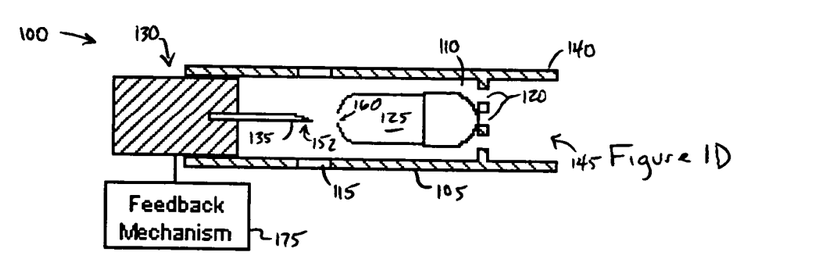
FIG. 1D is a schematic sectional side view of the version of an aerosolization apparatus shown in FIG. 1A just after capsule puncture.

To use the aerosolization apparatus 100, the pharmaceutical formulation in the capsule 125 is exposed to allow it to be aerosolized. In the version of FIGS. 1A though 1E, the puncture mechanism 130 is advanced within the chamber 110 by applying a force 150 to the puncture mechanism 130. For example, a user may press against a surface 155 of the puncturing mechanism 130 to cause the puncturing mechanism 130 to slide within the housing 105 so that the puncture member 135 contacts the capsule 125 in the chamber 110, as shown in FIG. 1B. By continuing to apply the force 150, the puncture member 135 is advanced into and through the wall of the capsule 125, as shown in FIG. 1C. The puncture member may comprise one or more sharpened tips 152 to facilitate the advancement through the wall of the capsule 125. The puncturing mechanism 130 is then retracted to the position shown in FIG. 1D, leaving an opening 160 through the wall of the capsule 125 to expose the pharmaceutical formulation in the capsule 125.

Figure 1E:
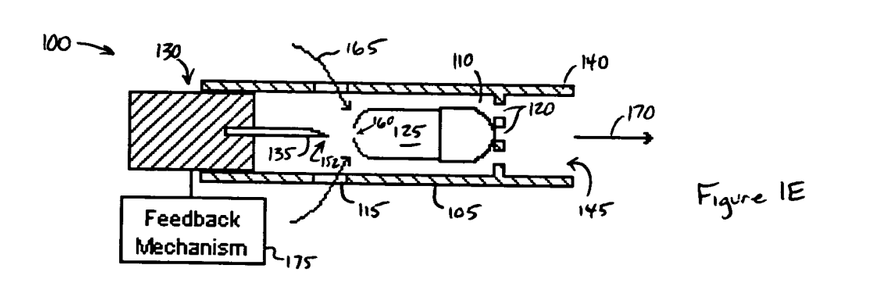
FIG. 1E is a schematic sectional side view of the version of an aerosolization apparatus shown in FIG. 1A in use.

Air or other gas then flows through an inlet 115, as shown by arrows 165 in FIG. 1E. The flow of air causes the pharmaceutical formulation to be aerosolized. When the user inhales 170 through the end section 140 the aerosolized pharmaceutical formulation is delivered to the user's respiratory tract. In one version, the air flow 165 may be caused by the user's inhalation 170. In another version, compressed air or other gas may be ejected into the inlet 115 to cause the aerosolizing air flow 165.

Proper creation of the opening 160 in the capsule 125 allows for efficient and effective delivery of the aerosolized pharmaceutical formulation to the user. In contrast, improper creation of the opening 160 can lead to inefficient and less effective delivery of the medicament to a user. For example, when the puncture member 135 is not advanced to a position where the wall of the capsule 125 is sufficiently penetrated, the opening may be too small to allow for sufficient amounts of the pharmaceutical formulation to be aerosolized. This can result in the amount of pharmaceutical formulation that is delivered to the user being less than the desirable dosage. In addition, advancing the puncture member 135 too far may also be undesirable. For example, when the puncture member 135 is advanced too far into the capsule, the puncture member 135 may contact the pharmaceutical formulation within the capsule 125 and cause damage or agglomeration of the pharmaceutical formulation. Also, the portion of the wall of the capsule 125 that is removed to create the opening 160 may become broken off from the capsule 125 becoming one or more loose fragments when excessive advancement occurs. These fragments may then be inhaled by the user, potentially causing discomfort. In some instances, over insertion of the puncturing member 135 can cause the shaft of the puncturing member 135 to contact the sides of the opening 160 during retraction of the puncturing member 135. This contact may lead to the capsule being pulled back into the chamber and/or may prevent the puncture member 135 from being retracted out of the capsule 125.

Accordingly, to increase efficiency and effectiveness, the aerosolization apparatus 100 of the present invention comprises a feedback mechanism 175 to provide an indication to a user when the puncturing member 135 has been moved to a predetermined position. For example, the feedback mechanism 175 may provide an indication 180 to the user when the puncture member 135 has advanced to the position shown in FIG. 1C. When the user receives the indication 180, the user will be alerted to the fact that the puncture member 135 has been advanced to a position where it creates a desirably large opening 160 into the capsule 125. In response to the indication 180 the user may stop the application of force 150, thereby preventing over advancement of the puncture member 135. The feedback mechanism 175 is particularly useful when the puncture member 135 has one or more sharpened tips 152 that easily penetrate the walls of the capsule 125 because the penetration may sometimes be undetectable by the user.

The indication 180 may be in delivered to the user through one or more of the user's sensory channels. For example, the indication 180 may be one or more of an audible, visual, or tactile signal. The indication 180 may be in response to an electronic signal or may be generated mechanically. In an electronic version, an electronic position detector, such as an optical encoder, may be provided to electronically detect the position of the puncture member 135. In such an embodiment, a controller may also be provided that receives the signal from the position detector and that generates an output signal that causes the actuation of the indication 180.

In one version, the feedback mechanism 175 is a mechanical system that provides a tactile sensation as the indication 180. This version is particularly effective in allowing the user to precisely control the operation of the aerosolization apparatus 100. For example, the tactile sensation may be provided through the puncturing mechanism 130. Accordingly, the user may apply the force 150 to the surface 155 of the puncturing mechanism 130, and the user may be provided with a tactile sensation through the same surface 155. In this way, the user's output force 150 and input sensation are delivered and received at the same sensory location. This often allows for a quicker response time by the user. Thus, as the user is pressing against the surface 155, as soon as the indication 180 is received at the surface 155, the user can stop the application of force 150.

A version of an aerosolization apparatus 100 comprising a feedback mechanism 175 which provides tactile feedback to the user is shown in FIGS. 2A through 2E. In this version, the housing 105 of the aerosolization apparatus 100 comprises a body 205 and a removable endpiece 210. The endpiece 210 may be removed from the body 205 to insert a capsule 125 in the chamber 110 which is formed when the body 205 and the endpiece 210 are connected together. The endpiece 210 comprises a partition 215 that blocks the forward end of the chamber 110, and the partition 215 has the one or more outlets 120 extending therethrough. An example of an aerosolization apparatus with a partition 215 and chamber 110 are described in U.S. Pat. No. 4,069,819 and in U.S. Pat. No. 4,995,385, both of which are incorporated herein by reference in their entireties. In such an arrangement, the chamber 110 comprises a longitudinal axis that lies generally in the inhalation direction, and the capsule 125 is insertable lengthwise into the chamber 110 so that the capsule's longitudinal axis may be parallel to the longitudinal axis of the chamber 110. In the version of FIGS. 2A through 2E, the chamber 110 is sized to receive a capsule 125 containing a pharmaceutical formulation in a manner which allows the capsule to move within the chamber 110. The inlets 115 comprise a plurality of tangentially oriented slots 220. When a user inhales 170 through the endpiece 210, outside air is caused to flow through the tangential slots 220 as shown by arrows 225 in FIG. 2E. This airflow 225 creates a swirling airflow within the chamber 110. The swirling airflow causes the capsule 125 to contact the partition 215 and then to move within the chamber 110 in a manner that causes the pharmaceutical formulation to exit the capsule 125 and become entrained within the swirling airflow. In one version, the capsule 125 may rotate within the chamber 110 in a manner where the longitudinal axis of the capsule is remains at an angle less than 80 degrees, and preferably less than 45 degrees from the longitudinal axis of the chamber. The movement of the capsule 125 in the chamber 110 may be caused by the width of the chamber 110 being less than the length of the capsule 125. In one specific version, the chamber 110 comprises a tapered section 230 that terminates at an edge 235. During the flow of swirling air in the chamber 110, the forward end of the capsule 125 contacts and rests on the partition 215 and a sidewall of the capsule 125 contacts the edge 235 and slides and/or rotates along the edge 235. This motion of the capsule is particularly effective in forcing a large amount of the pharmaceutical formulation through one or more openings 160 in the rear of the capsule 125.

Figure 2A:
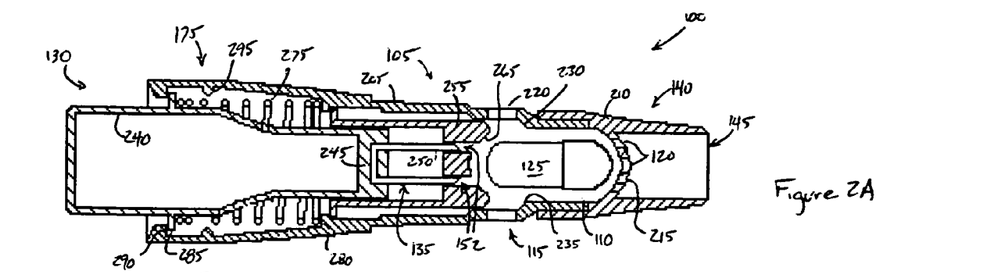
FIG. 2A is a schematic sectional side view of another version of an aerosolization apparatus in a rest position.
Figure 2B:
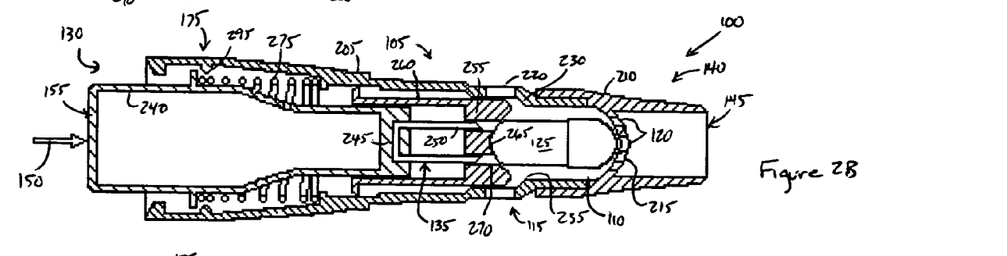
FIG. 2B is a schematic sectional side view of the version of an aerosolization apparatus shown in FIG. 2A just before capsule puncture.
Figure 2C:
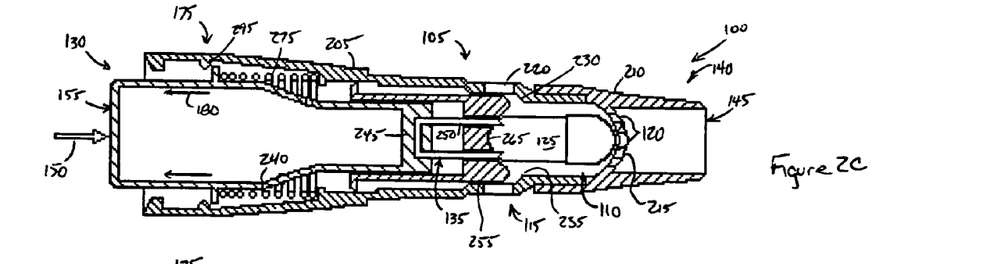
FIG. 2C is a schematic sectional side view of the version of an aerosolization apparatus shown in FIG. 2A as the capsule is being punctured.
Figure 2D:
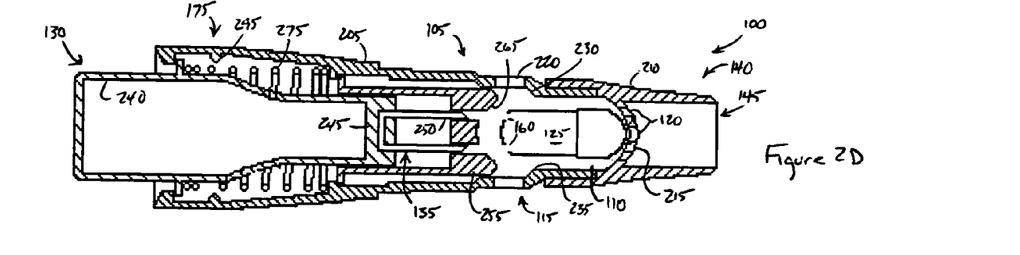
FIG. 2D is a schematic sectional side view of the version of an aerosolization apparatus shown in FIG. 2A just after capsule puncture.
Figure 2E:
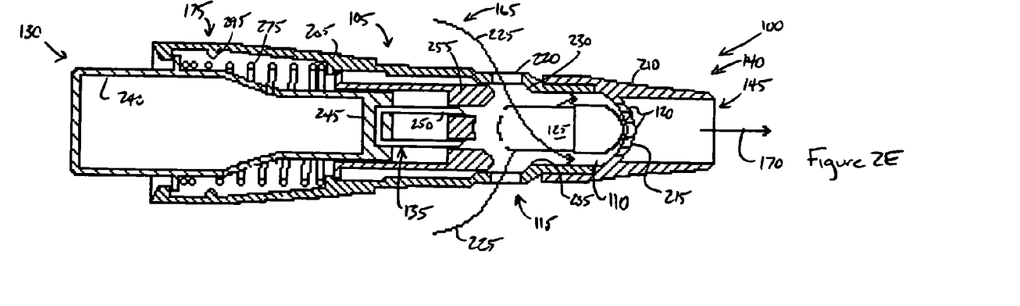
FIG. 2E is a schematic sectional side view of the version of an aerosolization apparatus shown in FIG. 2A in use.

The one or more openings 160 in the rear of the capsule 125 in the version of FIGS. 2A through 2E are created by a puncturing mechanism 130 that is slidable within the body 205. The puncturing mechanism 130, shown in its rest position in FIG. 2A, comprises a plunger 240 attached at its forward end 245 to the puncture member 135, which in the version shown is a U-shaped staple 250 having two sharpened tips 152. The puncturing mechanism 130 further comprises a seating member 255 which contacts the plunger 240 and/or the puncture member 135 and is slidable relative to the plunger 240 and the puncture member 135. To create the openings 160 in the capsule 125, the user applies a force 150 to the plunger 240, as shown in FIG. 2B, such as by pressing against the end surface 155 of the plunger 240 with the user's finger or thumb. The force 150 causes the plunger to slide within the body 205. A slight frictional contact between the plunger 240 the a rear section 260 of the seating member 255 causes the seating member 255 to also slide within the body 205 until a forward seating surface 265 of the seating member 255 contacts the capsule 125, as shown in FIG. 2B. The forward seating surface 265, which may be shaped to generally match the shape of the capsule 125, secures the capsule 125 between the seating member 255 and the partition 215. The continued application of force 150 causes the plunger 240 and the puncture member 135 to slide relative to the seating member 255, as shown in FIG. 2C, to advance the puncture member 135 through openings 270 in the forward seating surface 265 and into the capsule 125. Upon the removal of the force 150, a spring 275 or other biasing member urges the puncturing mechanism 130 back to its rest position. For example, the spring 275 may contact a shoulder 280 in the body 205 and press a flange 285 on the plunger 240 toward a rim 290 in the body 205. The frictional engagement between the plunger 240 and the seating member 255 also returns the seating member 255 to its retracted position when the plunger is returned to its retracted position.

The aerosolization apparatus 100 of FIGS. 2A through 2E also comprises a feedback mechanism 175 that delivers an indication 180 to the user through a mechanical arrangement. For example, the feedback mechanism 175 may comprise a portion of the body 205 that engages a portion of the puncturing mechanism 130 in a manner that provides a tactile indication to the user. In one version, as shown in FIGS. 2A through 2E, the feedback mechanism 175 comprises a protrusion 295 on the body 205 that engages the flange 285 or other section of the plunger 240. In one version, the protrusion 295 comprises a rib that extends around all or a portion of the inner surface of the body 205. In moving the puncturing mechanism 130 from the position shown in FIG. 2A to the position shown in FIG. 2B, there is no tactile indication provided to the user. Then, in moving the puncturing mechanism 130 to the position of FIG. 2C, resistance is provided by the contact of the flange 285 and the protrusion 295. The resistance is overcome by continued force 150, and the puncturing mechanism 130 punctures the capsule 125. The resistance and the passage of the flange 285 beyond the protrusion 295 can be detected by the user as a tactile indication 180 that the capsule has been punctured. The protrusion 295 is positioned so that as the flange 285 passes over the protrusion 295, the puncture member 135 penetrates the capsule 125 a predetermined amount. Accordingly, the user is alerted that the puncture has occurred and can stop applying the force 150. In this way, excessive insertion is prevented. In another version, the arrangement may be reversed with the protrusion being on the plunger and the flange or other contacting member being on the body.

The feedback mechanism 175 of the type shown in FIGS. 2A through 2E offers additional advantages. For example, the flange 285 and protrusion 295 can aid in puncturing the capsule 125. When the resistance between the flange 285 and the protrusion 295 is overcome, an extra force and/or a quick advancement of the puncturing mechanism 135 may occur. This extra force and/or quick advancement can provide improved penetration of the wall of the capsule 125. In addition, the tactile sensation provided by the feedback mechanism 175 is particularly useful for users with reduced hand and/or finger strength. The weakened users can continue to apply force 150 until the tactile feedback is received. Without the feedback, the user would not be confident that the capsule 125 is sufficiently and properly opened.

Figure 3A:
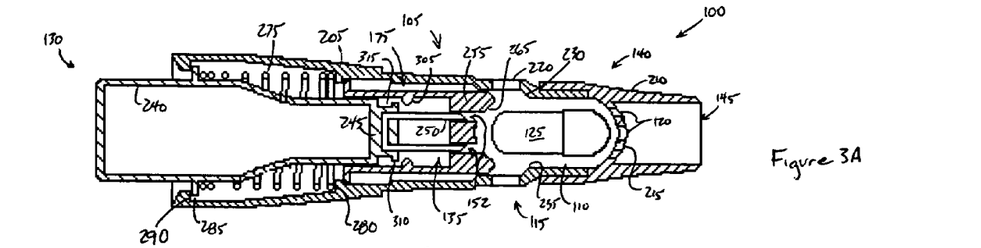
FIG. 3A is a schematic sectional side view of another version of an aerosolization apparatus in a rest position.
Figure 3B:
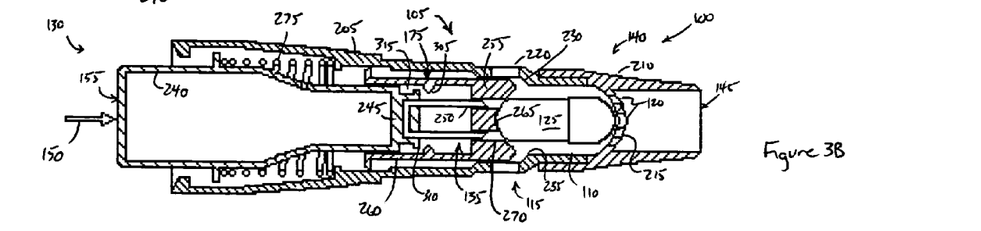
FIG. 3B is a schematic sectional side view of the version of an aerosolization apparatus shown in FIG. 3A just before capsule puncture.

In another version of an aerosolization apparatus 100, the feedback mechanism 175 may be provided within the puncturing mechanism 130. For example, FIGS. 3A through 3E show the operation of an aerosolization apparatus 100 similar to the one shown in FIGS. 2A through 2E, but with the feedback mechanism 175 being self-contained within the puncturing mechanism 130. In this version, a protrusion 305 is provided on the seating member 255. The protrusion 305 is provided on a surface of the seating member 255 that engages the plunger 240. A flange 310 on the plunger 240 contacts the protrusion 305 in a manner similar to the contact between the flange 285 and plunger 295 in the version of FIGS. 2A through 2E. Accordingly, after the seating member 255 is seated against the capsule 125, as shown in FIG. 3B, the seating member 255 is stationary within the body 205 during continued application of force 150. The continued application of force 150 advances the plunger 240 and puncture member 135 relative to the seating member 255. The protrusion 305 is positioned so as to provide a tactile sensation at the time of a predetermined amount of capsule puncture by the puncture member 130.

Figure 3C:
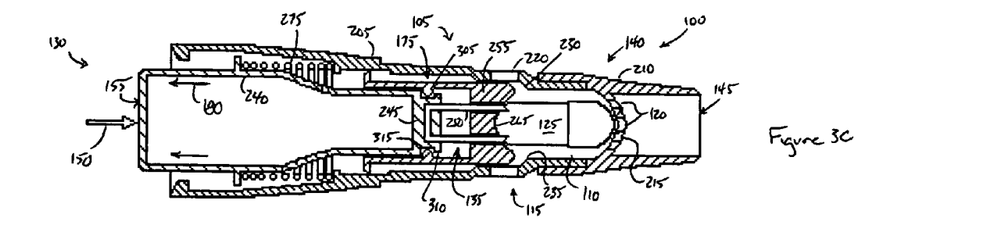
FIG. 3C is a schematic sectional side view of the version of an aerosolization apparatus shown in FIG. 3A as the capsule is being punctured.
Figure 3D:
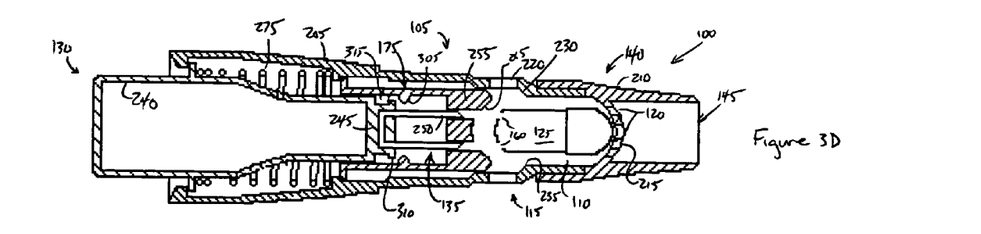
FIG. 3D is a schematic sectional side view of the version of an aerosolization apparatus shown in FIG. 3A just after capsule puncture.
Figure 3E:
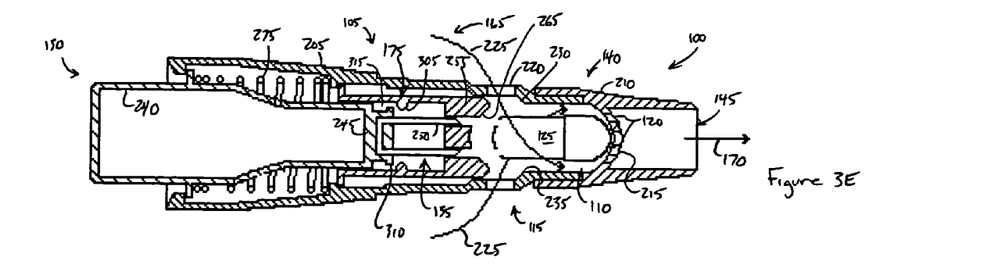
FIG. 3E is a schematic sectional side view of the version of an aerosolization apparatus shown in FIG. 3A in use.
Figure 4A:
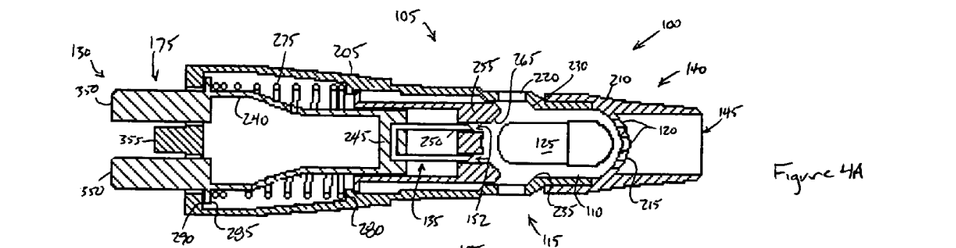
FIG. 4A is a schematic sectional side view of a version of an aerosolization apparatus in a rest position.
Figure 4B:
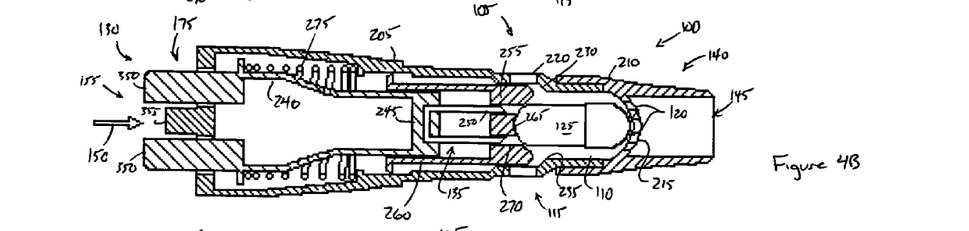
FIG. 4B is a schematic sectional side view of the version of an aerosolization apparatus shown in FIG. 4A just before capsule puncture.
Figure 4C:
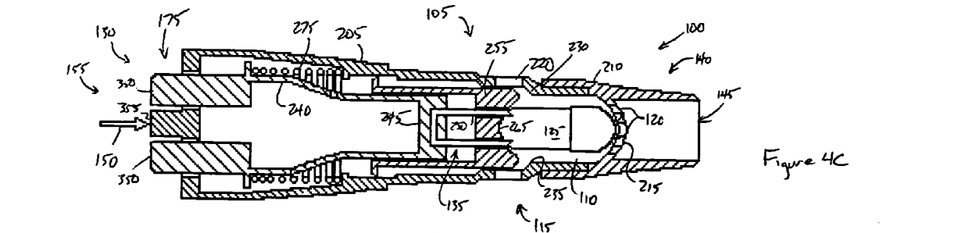
FIG. 4C is a schematic sectional side view of the version of an aerosolization apparatus shown in FIG. 4A as the capsule is being punctured.
Figure 4D:
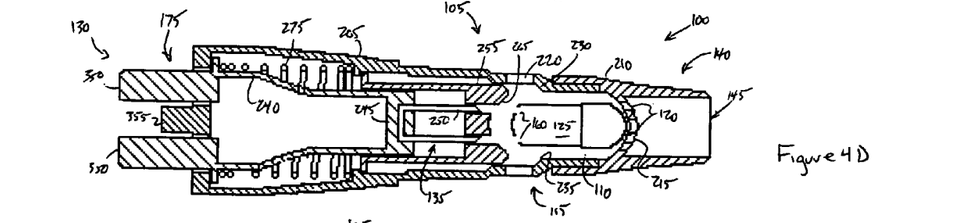
FIG. 4D is a schematic sectional side view of the version of an aerosolization apparatus shown in FIG. 4A just after capsule puncture.
Figure 4E:
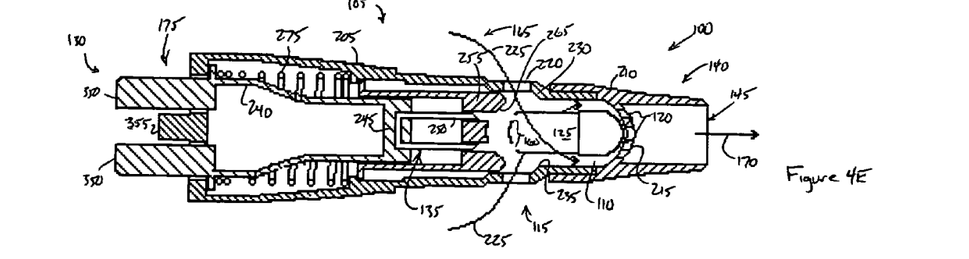
FIG. 4E is a schematic sectional side view of the version of an aerosolization apparatus shown in FIG. 4A in use.

The version of FIGS. 3A through 3E offers the advantages of the version of FIGS. 2A through 2E and additional advantages. For example, the contact between the protrusion 305 and the flange 310 can provide beneficial frictional contact. By pressing against the protrusion 305, the plunger 240 can more effectively move the seating member 255 from the position shown in FIG. 3A to the position shown in FIG. 3B and can more effectively retract the seating member 255 from the position shown in FIG. 3C to the position shown in FIG. 3D. In addition, in one version, a recess 315 may be provided for receiving the protrusion 305 after the tactile sensation is provided, as shown in FIG. 3C. In this version, a rear wall of the recess 315 engages the protrusion 305 to prevent the further insertion of the plunger 240. Therefore, this version provides both a tactile indication of proper penetration and a prevention of over penetration.

Another version of an aerosolization apparatus 100 with a feedback mechanism 175 is shown in FIGS. 4A through 4E. In this version, a portion of the apparatus becomes contactable by a user only when the puncturing mechanism 130 has been advanced the predetermined amount. For example, the plunger 240 may comprise two spaced apart surfaces 350 against which a user may press his or her finger or thumb. Between the surfaces 350 is a surface 355 of the body that is contacted by the finger or thumb only when the plunger 240 has been advanced a predetermined amount, such as to the position shown in FIG. 4C. By contacting the surface 355 the user is provided a tactile indication that the capsule 125 has been punctured.

In another version, the aerosolization apparatus 100 may be configured differently than as shown in FIGS. 2A through 2D, 3A through 3E, and 4A through 4E. For example, the chamber 100 may be sized and shaped to receive the capsule 125 so that the capsule 125 is orthogonal to the inhalation direction, as described in U.S. Pat. No. 3,991,761. As also described in U.S. Pat. No. 3,991,761, the puncturing mechanism 130 may puncture both ends of the capsule 125. In such version, a feedback mechanism 175 may be provided to indicate the puncture of one or both ends of the capsule 125. In another version, the chamber may receive the capsule 125 in a manner where air flows through the capsule 125 as described for example in U.S. Pat. No. 4,338,931 and in U.S. Pat. No. 5,619,985. In another version, the aerosolization of the pharmaceutical formulation may be accomplished by pressurized gas flowing through the inlets, as described for example in U.S. Pat. Nos. 5,458,135, 5,785,049, and 6,257,233, or propellant, as described in PCT Publication WO 00/72904 and U.S. Pat. No. 4,114,615. All of the above references being incorporated herein by reference in their entireties.

In a preferred version, the invention provides a system and method for aerosolizing a pharmaceutical formulation and delivering the pharmaceutical formulation to the respiratory tract of the user, and in particular to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, antiasthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight.

Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperature (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle.

The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

In one version, as discussed above, the pharmaceutical formulation may be contained within a capsule 125. The capsule 125 may be of a suitable shape, size, and material to contain the pharmaceutical formulation and to provide the pharmaceutical formulation in a usable condition. For example, the capsule may comprise a wall which comprises a material that does not adversely react with the pharmaceutical formulation. In addition, the wall may comprise a material that allows the capsule to be opened to allow the pharmaceutical formulation to be aerosolized. In one version, the wall comprises one or more of gelatin, hydroxypropyl methylcellulose (HPMC), polyethyleneglycol-compounded HPMC, hydroxyproplycellulose, agar, or the like. In one version, the capsule may comprise telescopically adjoining sections, as described for example in U.S. Pat. No. 4,247,066 which is incorporated herein by reference in its entirety. The size of the capsule may be selected to adequately contain the dose of the pharmaceutical formulation. The sizes generally range from size 5 to size 000 with the outer diameters ranging from about 4.91 mm to 9.97 mm, the heights ranging from about 11.10 mm to about 26.14 mm, and the volumes ranging from about 0.13 ml to about 1.37 ml, respectively. Suitable capsules are available commercially from, for example, Shionogi Qualicaps Co. in Nara, Japan and Capsugel in Greenwood, S.C. After filling, a top portion may be placed over the bottom portion to form the a capsule shape and to contain the powder within the capsule, as described in U.S. Pat. Nos. 4,846,876, 6,357,490, and in the PCT application WO 00/07572 published on Feb. 17, 2000, all of which are incorporated herein by reference in their entireties.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention.

Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. An aerosolization apparatus comprising:
   a housing defining a chamber having an air inlet and an air outlet, wherein the chamber is sized to receive a capsule containing a pharmaceutical formulation;
   a puncturing member moveable within the chamber to contact the capsule and to provide an opening in the capsule; and
   a feedback mechanism that provides a tactile indication to a user only when the puncturing member has been moved to a position where it provides the opening into the capsule,
   wherein the puncture member may be advanced beyond the position where it provides the opening into the capsule,
   whereby when air flows through the inlet, the pharmaceutical formulation is aerosolized and the aerosolized pharmaceutical formulation is delivered through the outlet.

2. An apparatus according to claim 1 wherein the puncture member comprises a sharpened tip for penetrating a wall of the capsule.

3. An apparatus according to claim 1 wherein the puncture member comprises a pair of sharpened tips for penetrating a wall of the capsule.

4. An apparatus according to claim 1 wherein the puncture member is positioned to pierce only one end of the capsule.

5. An apparatus according to claim 1 wherein the feedback mechanism comprises a protrusion that is engageable by a flange to provide the tactile indication.

6. An apparatus according to claim 1 wherein the feedback mechanism comprises a portion of the housing that is engageable by the user only when the puncture member has moved to the position where it provides the opening into the capsule.

7. An apparatus according to claim 1 wherein the chamber is elongated and has a longitudinal axis, and wherein the longitudinal axis of the chamber and the longitudinal axis of the capsule form an angle of less than about 45 degrees during use.

8. An apparatus according to claim 1 wherein the chamber is elongated and wherein the capsule is received lengthwise within the elongated chamber.

9. An aerosolization apparatus according to claim 1 wherein the width of the chamber is less than the length of the capsule.

10. An aerosolization apparatus comprising:
    a body defining a chamber having an air inlet and an air outlet, wherein the chamber is sized to receive a capsule containing a pharmaceutical formulation in a manner which allows the capsule to move within the chamber;
    a puncturing member moveable within the chamber to contact the capsule and to provide an opening in the capsule; and
    a feedback mechanism that provides a tactile indication to a user only when the puncturing member has been moved to a predetermined position,
    wherein the puncturing member is movable beyond the predetermined position,
    whereby when a user inhales, air enters into the chamber through the inlet so that the pharmaceutical formulation is aerosolized within the chamber and the aerosolized pharmaceutical formulation is delivered to the user through the outlet.

11. An apparatus according to claim 10 wherein the feedback mechanism provides the indication when the puncture member has been moved from a rest position to a capsule piercing position.

12. An apparatus according to claim 11 wherein the puncture member may be advanced beyond the capsule piercing position.

13. An apparatus according to claim 10 wherein the puncture member comprises a sharpened tip for penetrating a wall of the capsule.

14. An apparatus according to claim 10 wherein the puncture member comprises a pair of sharpened tips for penetrating a wall of the capsule.

15. An apparatus according to claim 10 wherein the puncture member is positioned to pierce only one end of the capsule.

16. An apparatus according to claim 10 wherein the feedback mechanism comprises a protrusion that is engageable by a flange to provide the tactile indication.

17. An apparatus according to claim 10 wherein the feedback mechanism comprises a portion of the housing that is engageable by the user only when the puncture member has moved to the predetermined position.

18. An apparatus according to claim 10 wherein the chamber is elongated and has a longitudinal axis, and wherein the longitudinal axis of the chamber and the longitudinal axis of the capsule form an angle of less than about 45 degrees during use.

19. An apparatus according to claim 10 wherein the chamber is elongated and wherein the capsule is received lengthwise within the elongated chamber.

20. An aerosolization apparatus according to claim 10 wherein the width of the chamber is less than the length of the capsule.

21. A method of providing an aerosolized pharmaceutical formulation, the method comprising:
providing an aerosolization apparatus comprising a housing which defines a chamber, the chamber being sized to receive a capsule containing a pharmaceutical formulation, the aerosolization apparatus further comprising a feedback mechanism that provides a tactile indication to a user only when the capsule has been punctured thereby allowing a user to stop the puncturing process by removing the application of force; and aerosolizing the pharmaceutical formulation when a user inhales by causing air to flow through an inlet in the housing, within the chamber, and through an outlet in the housing to provide the aerosolized pharmaceutical formulation to the user.

22. A method according to claim 21 wherein the housing comprises a body and an endpiece, the body and endpiece being connectable.

23. A method of aerosolizing a pharmaceutical formulation, the method comprising:

providing a capsule containing a pharmaceutical formulation in a chamber in a housing;

advancing a puncture member to create an opening in the capsule;

receiving a tactile indication from a feedback mechanism only when the opening in the capsule is created;

stopping the advancement by removing the application of force in response to receiving the indication; and inhaling through an opening in the housing to cause air to flow into the chamber through an inlet in the housing thereby aerosolizing the pharmaceutical formulation.

24. A method according to claim 23 wherein the chamber is elongated and wherein the capsule is inserted lengthwise into the elongated chamber.

* * * * *